United States Patent [19]

Veit

[11] Patent Number: 4,514,404
[45] Date of Patent: Apr. 30, 1985

[54] PROCESS FOR OBTAINING COMPLEX OF 3-METHOXY-N-METHYLMORPHINAN WITH 7-THEOPHYLLINEACETIC ACID (1:2)

[75] Inventor: Dagmar V. Veit, Barcelona, Spain

[73] Assignee: Prodes, S.A., Barcelona, Spain

[21] Appl. No.: 552,677

[22] Filed: Nov. 17, 1983

[30] Foreign Application Priority Data

Nov. 19, 1982 [ES] Spain ............................ 517.500

[51] Int. Cl.$^3$ .................. C07D 473/04; A61K 31/52
[52] U.S. Cl. .................................. 514/265; 544/267; 544/268; 546/74

[58] Field of Search .............. 544/266, 268, 267; 546/74; 424/253

[56] References Cited

U.S. PATENT DOCUMENTS 2,676,177  4/1954  Schnider et al. .................. 546/74
3,466,277  9/1969  Merz et al. ...................... 544/268

Primary Examiner—Nicholas S. Rizzo
Attorney, Agent, or Firm—Flynn, Thiel, Boutell & Tanis

[57] ABSTRACT

A complex of 3-methoxy-N-methylmorphinan with 7-theophyllineacetic acid (1:2) is prepared by reacting the reactive materials in a polar solvent. The complex has antitussive activity.

5 Claims, No Drawings

PROCESS FOR OBTAINING COMPLEX OF 3-METHOXY-N-METHYLMORPHINAN WITH 7-THEOPHYLLINEACETIC ACID (1:2)

The present invention relates to a process of preparing a complex of 3-methoxy-N-methylmorphinan with 7-theophyllineacetic acid. This complex contains 2 moles of 7-theophyllineacetic acid per one mole of 3-methoxy-N-methylmorphinan. The complex has the following formula:

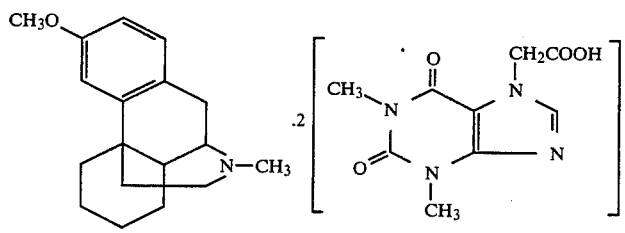

The complex according to the present invention is sometimes hereinafter referred to as "Theophane."

This complex, obtained by the process described in the present invention, has a defined composition formed by 1 mole of 3-methoxy-N-methylmorphinan and 2 moles of 7-theophyllineacetic acid. This complex is a stable product with physical properties and spectroscopic data which prove that it is a complex of a defined structure, completely different from a simple mixture of 1 mole of 3-methoxy-N-methylmorphinan and 2 moles of 7-theophyllineacetic acid.

The process comprises reacting, in a suitable solvent, 3-methoxy-N-methylmorphinan with 7-theophyllineacetic acid.

Suitable solvents are polar solvents such as, for instance, acetonitrile and alcohols, preferably isobutanol.

The amount of 7-theophyllineacetic acid used in the reaction, with respect to 1 mole of 3-methoxy-N-methylmorphinan, can vary from 1 and 1.15 moles.

The complex is crystallized by cooling the reaction mass, thereby obtaining unique crystals having a melting point of from 187° to 189° C. The fact that there is formed a chemical complex of a defined structure, different from a mixture of the two components, is free from any doubt and is established by the hereundermentioned experimental data:

The product is always formed with a defined molar proportion (1:2) of the constituents, as shown by the quantitative analysis of the same.

The product melts at a fixed temperature (187° to 189° C.), while a simple mixture of the components would melt over a large temperature range (100° to 207° C.).

The infrared spectrum of the complex is different from that of the mixture, in regard to the intensity as well as the form and position of the most significant bands.

The product observed under a microscope is formed by a single type of crystal, whereas in the mixture of the two components there can be observed two clearly differentiated types of crystals.

Finally and as the most compelling proof that the product of the invention is a stable complex of a defined composition, the diffraction spectrum of the product of the invention shows diffraction maxima which are totally different in comparison with the ones of the crystalline species of 7-theophyllineacetic acid and 3-methoxy-N-methylmorphinan, or of the mixture of both products in the molar ratio (1:2).

The compound, which is the subject of the present invention, has a potent antitussive activity. This activity has been compared with the activity of codeine and dextromethorphan by the experimental mode of Chen, J.Y.P. and col. (1960), consisting in exciting guinea pigs subjected to an atmosphere of sulfuric acid to cough.

There are used guinea pig males having a weight of 300–400 grs which are treated in respective lots, with codeine (40 mg/kg.; n=6), dextromethorphan (40 mg/kg.; n=6), theophane (20 mg/kg.; n=5) and theophane (40 mg/kg.; n=6), wherein "n" signifies the number of animals tested in the respective lots and the other data in the parentheses refers to the dosage amount, e.g. 40 mg/kg. The numbers of occurrences of coughing of each animal before and one hour after the oral administration of the drug are measured.

In Table I are detailed the results obtained by the experiment, before and after the administration of the drug as well as the percentage of inhibition of the cough.

TABLE I

| Drug | Animal No. | before | after | inhibition (%) | Average value |
|---|---|---|---|---|---|
| Codeine (40 mg/kg) | 1 | 7 | 2 | 71.4 | 92.2 ± 12.5 |
|  | 2 | 3 | 0 | 100.0 | (p < 0.001) |
|  | 3 | 11 | 2 | 81.8 |  |
|  | 4 | 3 | 0 | 100.0 |  |
|  | 5 | 9 | 0 | 100.0 |  |
|  | 6 | 3 | 0 | 100.0 |  |
| Dextromethorphan (40 mg/kg) | 1 | 6 | 4 | 33.3 | 69.7 ± 27.0 |
|  | 2 | 10 | 6 | 60.0 | (p < 0.005) |
|  | 3 | 3 | 0 | 100.0 |  |
|  | 4 | 4 | 1 | 75.0 |  |
|  | 5 | 2 | 1 | 50.0 |  |
|  | 6 | 3 | 0 | 100.0 |  |
| Theophane (20 mg/kg) | 1 | 6 | 4 | 33.3 | 44.35 ± 17.5 |
|  | 2 | 14 | 10 | 28.57 | (p < 0.005) |
|  | 3 | 6 | 4 | 33.3 |  |
|  | 4 | 3 | 1 | 66.6 |  |
|  | 5 | 5 | 2 | 60.0 |  |
| Theophane (40 mg/kg) | 1 | 5 | 2 | 60.0 | 70.5 ± 26.6 |
|  | 2 | 18 | 5 | 72.2 | (p < 0.005) |
|  | 3 | 13 | 9 | 30.7 |  |
|  | 4 | 3 | 0 | 100.0 |  |
|  | 5 | 10 | 4 | 60.0 |  |
|  | 6 | 5 | 0 | 100.0 |  |

From the results it is deduced that the compound of the present invention, administered orally at a dosage of 20 and 40 mg/kg, shows an antitussive activity which is significant with regard to its proper control. With a dosage of 40 mg/kg its effect is similar to the one produced by administering an equal amount of dextromethorphan which, referring to the weight index, means that theophane has a greater antitussive activity based on the 3-methoxy-N-methylmorphinan content.

The bronchodilatory activity "in vitro" of the compound of the present invention has been studied, using the method of tracheal chain of guinea pigs, described by J. C. Castillo and E. J. J. de Beer in Pharmacol.Expt. Therap., 90, 104. The trachea of male guinea pigs having a weight of 250-350 grs were extracted; then the rings are sectioned, always endeavoring that the trachea is bathed by the corresponding perfusion liquid and under oxygenation conditions for joining posteriorly the tracheal rings by means of a silk yarn forming the chain giving response to the drugs to be administered. The chain is placed in the bath of organs fixed to the registering arm of a chymograph. The bath is to be maintained at the constant temperature of 37.5° C. and using, as the liquid, the Krebs-Hanselett solution.

As a bronchoconstrictor drug, there is used histamine at a concentration of $1 \times 10^{-5}$ molar.

The bronchodilatory activity of theophane and theophylline have been compared, for various dosages, and the results obtained are presented in Table II.

TABLE II

| Dosage (MOLAR) | Activity (%) | |
|---|---|---|
| | Theophane | Theophylline |
| $1 \times 10^{-5}$ | 0 | 0 |
| $2 \times 10^{-5}$ | — | 6.25 |
| $5 \times 10^{-5}$ | 8.3 | — |
| $1 \times 10^{-4}$ | 54.6 | 10.378 |
| $2 \times 10^{-4}$ | 37.5 | 30 |
| $5 \times 10^{-4}$ | 85.3 | 59.1 |
| $1 \times 10^{-3}$ | 100 | 100 |

The theophane product of the present invention shows a bronchodilatory activity "in vitro" at lower concentrations than theophylline, although the elapsed time required to obtain the bronchodilatation is larger for theophane than for theophylline. At the dosge of $5 \times 10^{-4}$ molar, the time elapsed until obtaining an activity of 50% for theophane is of 280 seconds, while the time for theophylline is only of 180 seconds.

The acute toxicity of theophane has been studied orally and i.p. in the mouse and in the rat. The $LD_{50}$ and the limits of reliance have been determined by the technique of Litchfield and Wilcoxon. Table III summarizes the values of the obtained $LD_{50}$, as well as of $LD_0$.

TABLE III

| Species | VIA | $LD_{50}$ (mg/kg) | $LD_0$ (mg/kg) |
|---|---|---|---|
| RAT | Oral | 574.28 / 429.21 \ 302.78 | 204.4 |
| | I.P. | 262.36 / 229.94 \ 201.50 | 156.4 |
| MOUSE | Oral | 435.30 / 359.70 \ 297.30 | 182.2 |
| | I.P. | 162.60 / 141.81 \ 113.60 | 102.3 |

The subacute toxicity of theophane has been studied after repeated oral administrations over a period of 1 month in Wistar rats of both sexes. The theophane dosage used was 20 mg/kg/day, 60 mg/kg/day and 120 mg/kg/day. One lot of control animals received only excipient. The evolution of mortality, weight rates, diet consumption, hematic, biochemical and urinary parameters, as well as the histopathologic study showed the null toxicity of the theophane product at the dosages used.

The fetal and teratogenous toxicity of theophane studied in Sprague-Dawley rats and fetuses of the first generation, and using a dosage of 20, 65 and 130 mg/kg/day of the product via oral administration and during the period of organogenesis, has shown that the product of the present invention does not produce toxic effects to the gestating females and their offspring and also does not induce teratogenous effects.

The possible mutagenic effect of theophane has been evaluated according to the text described by Ames, B. N. and cols (1975) using auxotrophic *S.typhimurium* strains for the histidine. The product has been studied at six different dosages, dissolved in DMSO, and in the presence and absence of a system of metabolic activation and in front of positive controls. No reversion increase could be observed, consequently the conclusion is that theophane does not have any mutagenic activity in any of the used bacterial strains.

The cardiovascular activity (technique of Smith, 1961) and the neuropharmacological activity (Irwin test) of the theophane product have been studied respectively in guinea pigs and rats (males). Increasing concentrations of from 0.5 to 10 mg/kg of theophane do not produce effects on the cardiovascular system. In the Irwin test, dosages of 60 mg/kg of theophane produced similar depressor effects as those caused by dextromethorphan administered at the dosage of 40 mg/kg.

The compound subject of the present invention can be used in human therapy. The daily dosage via oral administration is from 80 mg to 160 mg. It can be administered in the form of tablets, capsules, syrup and suppositories.

Hereunder are given some examples of pharmaceutical dosage forms for administering theophane:

| Formula for tablets: | |
|---|---|
| Theophane | 20 mg |
| Lactose | 40 mg |
| Starch | 20 mg |
| Aerosil P-101 | 63 mg |
| Magnesium stearate | 1.2 mg |
| Ac.di.sol | 5 mg |
| Formula for syrup: | |
| Theophane | 600 mg |
| Propylene glycol | 25 mg |
| Glycerol | 20 mg |
| Tween 20 | 5 mg |
| Water c.s.p. | 150 mg |
| Formula for suppositories: | |
| Theophane | 30 mg |
| Monolene I.M.-9 | 2.470 gr |

To facilitate this disclosure, the following examples describe illustrative ways of preparing the compound according to the invention. These examples are given for illustrative purposes only and the invention is not limited thereto.

EXAMPLE 1

27.1406 gr (0.100 moles) of 3-methoxy-N-methylmorphinan (mp=109°-116° C.) are dissolved under heating, in 100 ml isobutanol, adding 27.5731 gr (0.115 moles) of 7-theophyllineacetic acid (mp=271° C.). The obtained solution is then cooled to 5° C. during 24 hours. It is filtered and washed with 20 ml of cold isobutanol. There are obtained 17.3 gr (yield: 40%) of complex of mp=187°–90° C.

Calc. ($C_{36}H_{45}N_9O_9$): 57.82%, C; 6.06%, H; 16.85%, N. Found: 57.70%, C; 6.15%, H; 16.94%, N.

The valuation of the components resulted in a determination of 36.3% of 3-methoxy-N-methylmorphinan and 63.7% of 7-theophyllineacetic acid, corresponding to a molar proportion of 1:2.

The infrared spectrum (KBr) showed among others the following bands: 3520, 3300, 3120, 3000, 2930, 2860, 1700, 1660, 1545, 1460 and 1240 cm$^{-1}$.

UV spectrum $\lambda_{max.}$=273 nm.

$^1$HNMR Spectrum (DMSO d$_6$, δppm) 2.5(s) 3.0(s); 3.2(s) 4.1(s) 4.65(s) 6.5 and 6.7 (AB system), 7.65(s).

Diffraction Spectrum of X-rays (reticular space d$_{hkl}$ Å):

| | | | | | |
|---|---|---|---|---|---|
| 14.9393 | 12.0341 | 9.7040 | 7.3232 | 6.8699 | 6.7483 |
| 6.1899 | 5.9829 | 5.3250 | 5.1474 | 4.9347 | 4.8350 |
| 4.4701 | 4.2323 | 4.0192 | 3.8759 | 3.7990 | 3.7090 |
| 3.5936 | 3.5441 | 3.5082 | 3.4321 | 3.3392 | 3.3085 |
| 3.2133 | 3.1243 | 3.1243 | 3.0714 | 2.9453 | 2.9057 |
| 2.7921 | 2.7269 | 2.7269 | 2.6378 | 2.5954 | 2.5214 |
| 2.4656 | 2.3523 | 2.2735 | 2.2102 | 2.1542 | 2.1111 |
| 2.0740 | 2.0340 | 1.8869 | 1.8614 | 1.7883 | 1.6708 |

EXAMPLE 2

1.3750 gr (0.005 moles) of 3-methoxy-N-methylmorphinan are dissolved in 10 ml of anhydrous acetonitrile, and 1.1910 gr (0.005 moles) of 7-theophyllineacetic acid are added. The reaction mixture is cooled to 0° C. and filtered. There are obtained 1.1217 gr (yield: 60%) of the complex in the form of white crystals having a mp=187°–9° C.

The spectroscopical data and physical constants of the obtained product coincide with those of the product obtained in Example 1.

The embodiments of the invention in which an exclusive property or privilege is claimed are defined as follows:

1. A process for preparing a complex of 3-methoxy-N-methylmorphinan with 7-theophyllineacetic acid (1:2), having the formula:

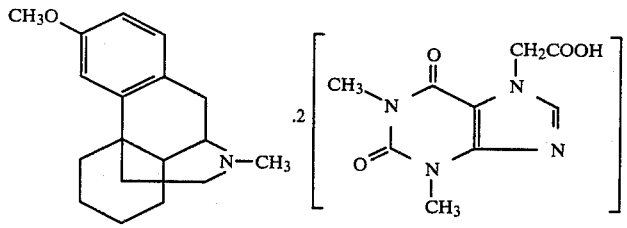

which comprises reacting, in a polar solvent, 3-methoxy-N-methylmorphinan with 7-theophyllineacetic acid, wherein the molar ratio of 7-theophyllineacetic acid to 3-methoxy-N-methylmorphinan is in the range of 1:1 to 1.15:1, to form a hot reaction mass; crystallizing said complex by cooling said reaction mass to a temperature in the range of 0° C. to 5° C., and then washing the recovered crystals of said complex.

2. A process according to claim 1, in which said polar solvent is isobutanol.

3. A complex of 3-methoxy-N-methylmorphinan with 7-theophyllineacetic acid having the formula

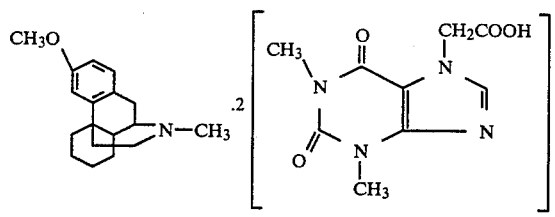

4. A pharmaceutical composition having antitussive activity comprising a therapeutically effective amount of a complex as claimed in claim 3, in combination with a pharmacologically acceptable vehicle.

5. A method of treating a patient to reduce coughing which comprises administering to the patient a pharmaceutical composition as claimed in claim 4.

* * * * *